United States Patent [19]

Kolenik

[11] 4,013,081
[45] Mar. 22, 1977

[54] PEDIATRIC CARDIAC PACER SYSTEM

[75] Inventor: Steve A. Kolenik, Leechburg, Pa.

[73] Assignee: ARCO Medical Products Company, Leechburg, Pa.

[22] Filed: Apr. 19, 1976

[21] Appl. No.: 678,265

[52] U.S. Cl. .......................... 128/419 P; 128/404; 128/419 PS

[51] Int. Cl.² ......................................... A61N 1/36

[58] Field of Search ... 128/419 P, 419 PG, 419 PS, 128/419 R, 421, 422, 423, 404, 419 C, 419 E

[56] References Cited

UNITED STATES PATENTS

| 3,598,128 | 8/1971 | Chardack | 128/419 P |
|---|---|---|---|
| 3,683,933 | 8/1972 | Mansfield | 128/419 P |
| 3,913,587 | 10/1975 | Newash | 128/419 P |
| 3,926,198 | 12/1975 | Kolenik | 128/419 P |

Primary Examiner—William E. Kamm
Attorney, Agent, or Firm—John R. Ewbank

[57] ABSTRACT

An infant grows rapidly enough that the distance between the heart and the location for the implantation of a cardiac pacer can change during the few years between surgical investigations of the implanted apparatus. The lead connecting the pacer with the heart follows a large spiral path around the pacer so that the spiral can tighten to a smaller spiral to accommodate the greater distance between the heart and the pacer as the infant grows. Such spiral portion of the lead is within a plastic bag permitting such contraction of the spiral without the lead adhering to tissue. The association of the plug at the end of the lead with the cylindrical socket in the end face of the pacer helps to direct the lead toward its initial large spiral path. Such socket is encapsulated in a plastic shield at one of the four corners of the two side faces of the pacer. Adequate battery life is achieved by one or more cells having the combination of a lithium anode and thionyl chloride-containing electrolyte. One embodiment of the pediatric pacer has dimensions of about 51 × 36 × 16 millimeters.

8 Claims, 4 Drawing Figures

PEDIATRIC CARDIAC PACER SYSTEM

FIELD OF INVENTION

This invention relates to a system using a pediatric cardiac pacer in children and a lead from the pacer to the heart, the path of the lead permitting automatic accommodation to the increasing distance between the pacer and the heart as the child grows.

PRIOR ART

Kolenik U.S. Pat. No. 3,926,198 describes a cardiac pacer having a plurality of electrochemical cells featuring a lithium anode and an electrolyte consisting predominantly of thionyl chloride. The Kolenik-type pacer was so much smaller than any previously offered pacer that its smallness permitted significant break-throughs in the utilization of pacers. Physicians have been discovering more and more types of cardiac problems among children which can be controlled more satisfactorily by the use of a cardiac pacer. However, notwithstanding the long standing demand for a pediatric pacing system, technologists heretofore have been unable to supply a pacer system having satisfactory characteristics and sufficient miniaturization to cope with some of the problems sometimes encountered in situations suggesting use of a pediatric pacer.

SUMMARY OF THE INVENTION

In accordance with the present invention the electrical conductor from the pacer is directed as a flat spiral around the pacer and the spiral portion of the lead is within a flat bag inhibiting any propensity of such portion of the electrical conductor to adhere to adjacent tissue. A cardiac pacer is radically miniaturized by utilizing a voltage source system occupying a cylindrical space having a diameter of about 14 millimeters and a length of about 24 millimeters, said voltage source featuring one or more electro chemical cells having a lithium anode and a thionyl chloride electrolyte. The size of an appropriate embodiment of the pacer can thus be reduced to about 51 × 36 × 16 mm.

The nature of the invention is further clarified by reference to descriptions of illustrative embodiments.

DESCRIPTIONS OF ILLUSTRATIVE EMBODIMENTS

Figure 1:
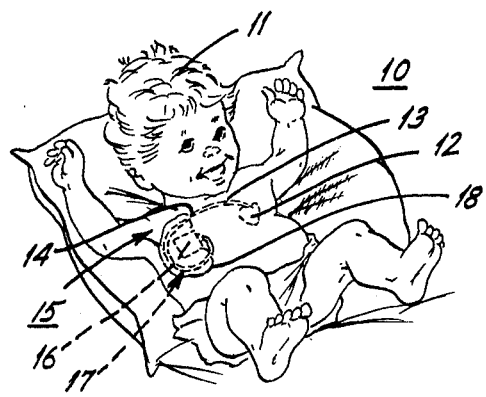
FIG. 1 is a schematic representation of an infant in whom is implanted a pediatric pacer system comprising a pacer connected to the heart through a lead directed through a spiral path.

A diagrammatic representation of a pediatric pacer system 10 is shown in FIG. 1. A child 11 has a signal zone 12 in its heart to and from which signals are transmitted through a normal zone 13 of an electrical conductor (generally designated as a lead) 14. Said normal zone 13 of lead 14 transmits signals between the signal zone 12 of heart and an implantation zone 15 for a cardiac pacer 16. In an adult, the distance between the implantation zone 15 and signal zone 12 of the heart generally remains substantially the same during the intervals between surgical investigations. Such intervals have typically been between about 1 and 3 years but recent improvements such as Kolenik U.S. Pat. No. 3,926,198 have suggested that such intervals might be extended to 10 to 17 years. In a child, the distance between the implantation zone 15 and signal zone of the heart can increase measurably during an interval as short as a year. Because the normal zone 13 of a lead 14 is not readily stretched, the growth of child 11 tends to impose an uprooting force on the normal zone 13 of the lead 14 at its contact with the signal zone 12 of the heart.

By the present invention, the normal zone 13 of lead 14 is automatically lengthened (notwithstanding the substantial nonstretchability of lead 14) as portions of lead 14 shift from a spiral portion 17 of lead into the normal zone 14 of lead.

Particular attention is directed to the shaping of a spiral portion 17 of the lead 14 into a spiral path around pacer 16, whereby the lead 14 can accommodate itself to the increasing distance between the implantation zone 15 and signal receiving zone 12 as the child 11 grows larger.

The tissue adjacent the electrical lead 14 tends to grow around such lead to anchor it in a particular path. In order to prevent such anchoring of the spiral portion 17 of lead 14 to nearby tissue, a bag 18 protects at least the spiral portion 17 of said lead 14. Said bag is positioned so that the spiral path 17 extends around a centrally located pacer 16. If desired, the shape of bag 18 can accommodate merely the spiral portion of lead 14. It is important that the electrical connection be maintained between a portion of pacer 16 and tissue in the implantation zone 15. Such can be done by shaping bag 18 to fit around about three sides of pacer 16 while keeping only the spiral portion 17 of lead within the bag 18.

At the time of implantation, the spiral portion 17 can follow a large spiral path but as the child grows larger and as the distance between the implantation zone 15 and signal zone 12 is lengthened, the spiral portion 17 within bag 18 accommodates itself by contracting so that the normal portion 13 is lengthened sufficiently to accommodate the growth of the child. Such contracting of the spiral path does not bend the lead about any radius so small as to kink or endanger the flexibility of lead 14.

Figure 2:
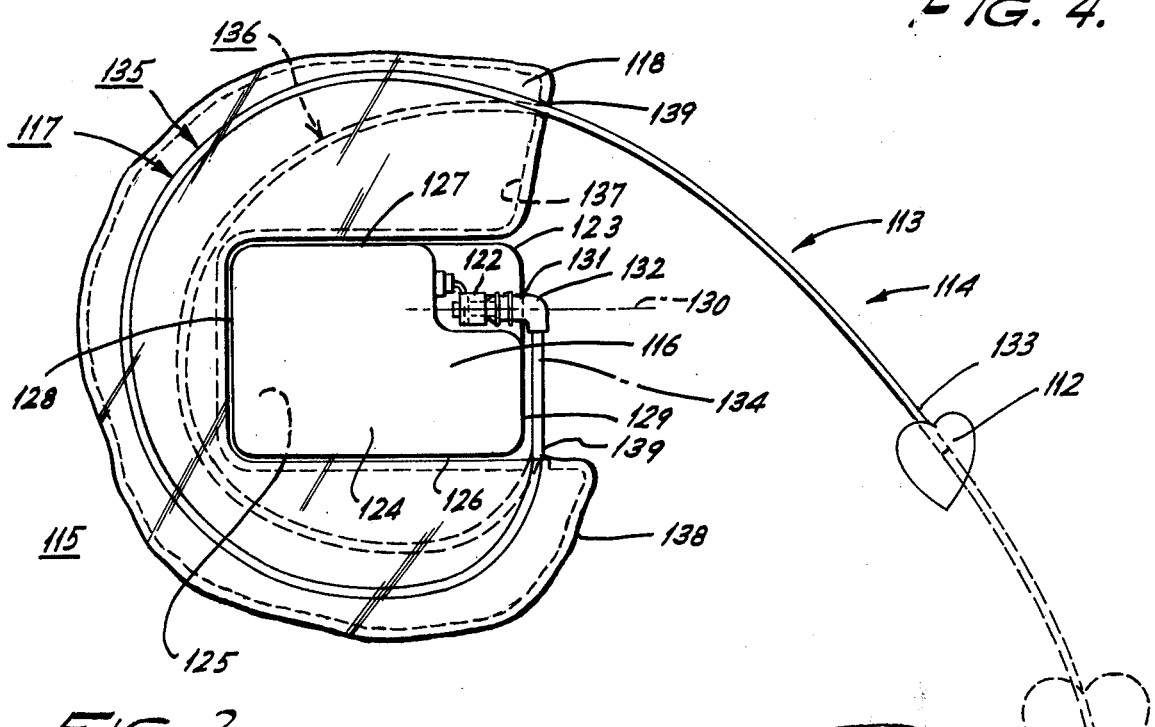
FIG. 2 is a schematic view of a portion of pacer system having an electrical conductor or lead directed as a spiral path around the pacer, the spiral portion of the lead having little propensity to anchor to body tissue because such spiral portion is protected within a plastic bag having internal surfaces inhibiting growth of tissue.

A pediatric pacer 116, as shown in FIG. 2, has a cylindrical socket 122 anchored within a plastic shield 123. Said pacer 116 has a shape resembling an orthagonal block having six faces comprising a pair of side faces 124, 125, a pair of support faces 126, 127, and a pair of end faces 128, 129. The socket 122 has a cylindrical well having an axis 130 forming a controlled angle 131 with respect to the end face 129 of the pacer 116. The combination of plug 132 and angle 131 controls the proximal zone of said spiral portion 117 of lead 114, urging the lead 114 toward such spiral path around the pacer. Such mechanical features help to control the path of the lead 114 so that it follows a spiral path around the pacer 116, the size of the spiral being significantly larger than the smallest spiral feasible in view of the restricted radius of curvature of the lead 114. As the body grows, thereby increasing the distance between the signal receiving zone 112 of the heart and the socket 122 of pacer 116, the spiral portion 117 of lead 114 contracts such spiral path, thereby permitting the lead to accommodate to such increasing distance.

As shown in FIG. 2, angle 131 is the conventional 90° and plug 132 is an elbow plug so that the path of lead 114 is parallel and adjacent end face 129 of pacer 116. Although elbow plugs have been previously employed for other electrical connectors, there has been widespread use of 180° plugs for leads connecting with cardiac pacers. Such elbow plug 132 cooperates with angle 131 in directing the proximal portion of lead 114 toward its spiral path instead of directly toward signal zone 112.

Lead 114 can be deemed to include a distal portion 133 associated with signal zone 112 of the heart, a normal portion 113 extending between signal zone 112 and implantation zone 115 (and automatically lengthened as the child grows); a spiral portion 117, and a proximal portion 134 associated with plug 132. At the time of implantation, the spiral portion 117 is shaped into a large spiral 135. As the child grows, and as more of the lead shifts into its normal portion 113, spiral portion 117 contracts into a smaller spiral 136 without developing a kink or troublesomely small bending radius less than the permissible resilient bending radius of the lead.

In order to decrease the likelihood of adhesion between tissue and the spiral portion 117 of lead 114, it is enclosed within a bag 118, the internal walls 137 of which are resistant to tissue growth. Said bag 118 can have one or more openings 139 for associating lead 114 with the system. The lead 114 can be shaped into a spiral prior to connecting the plug 132 to socket 122 of pacer 116. An opening 139 ordinarily assures a sliding fit with lead 114. Appropriate designs can help in minimizing flow of fluids between the inside of bag 118 and the zone of implantation 115. The bag 118 desirably includes a central vacancy so that the bag can fit around a pacer 116. The pacer 116 can be placed in its desired position during implantation and tissue growth can aid in stablizing the pacer position. The contraction of the spiral lead represents all of the movement within the bag. Shifting of the pacer 116 is minimized by the system of the present invention. The exterior surfaces 138 of bag 118 are desirably treated to accelerate growth of tissue and anchoring of the exterior bag walls to the tissue of the implanting zone. After the tissue has grown to anchor the exterior of the bag 118, the sliding fit between the exterior of the lead 114 and the opening 139 of the bag 118 is such that additional lead is pulled from the bag as the body grows. The flow of liquids between the inside of bag 118 and the zone of implantation is minimized by such sliding fit at opening 139.

A lead 114 can follow a path of a large spiral 135 when first implanted as shown schematically in FIG. 2. As the child grows, the distance between the heart and the pacer 116 is lengthened. The constant length lead 114 is able to maintain its connection with both the heart and pacer 116 because the lead accommodates to the lengthening distance by automatically contracting the large spiral 135 of FIG. 2 into a spiral of intermediate size and then to the small spiral 136. Such adaptability of lead 114 to adjust to the small spiral 136 path is attributable in part to the association of the angle 131 of the axis 130 of the well of cylindrical socket 122 with respect to end face 129 of pacer 116. The electrical connection can be maintained between the signal zone of the heart and the pacer 116 during a period in which the distance between the pacer and the signal zone of this heart is lengthened as the body of the child grows.

Figure 3:
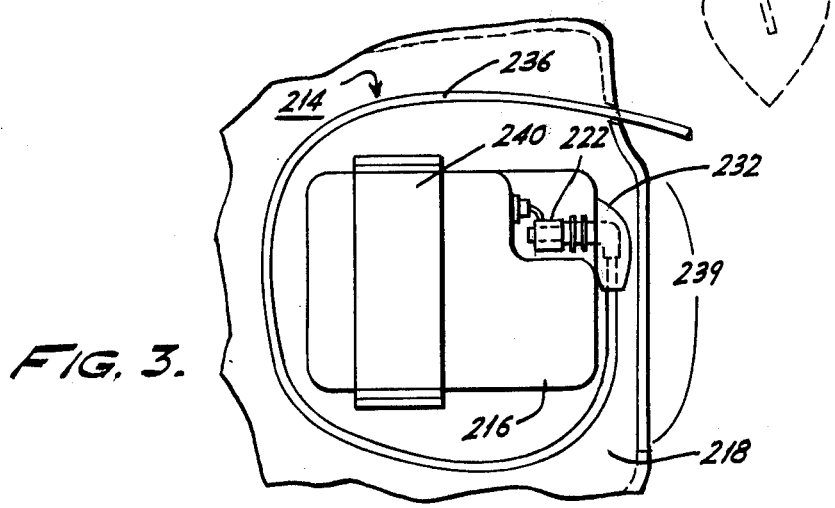
FIG. 3 is a schematic view of a portion of a pacer system comprising a bag accommodating both the pacer and the spiral path of the lead, the view showing the contracted spiral subsequent to significant growth of the patient.

As shown in FIG. 3 a pacer 216 supplies signals to a lead 214 which is following a small spiral path 236. A bag 218 has a large opening 239 into which pacer 216 and the lead in a spiral form can be placed. A cradle 240 serves to anchor the pacer 216 at the central area of bag 218.

Figure 4:
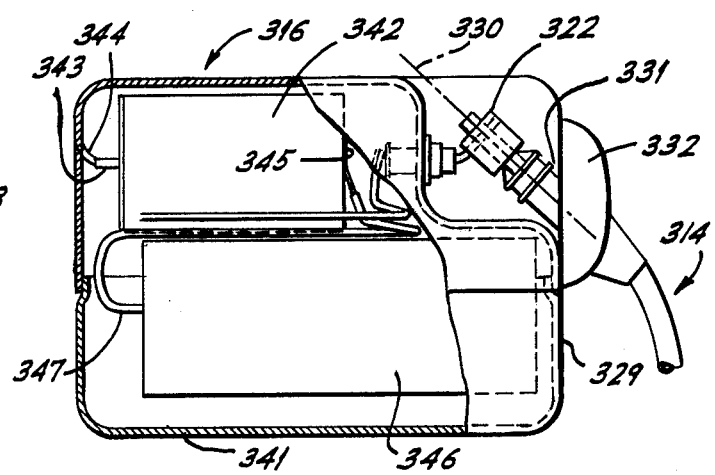
FIG. 4 is a partially cross section view of an alternative embodiment of a pediatric pacer wherein the angle of the axis of the socket helps to direct the lead toward its spiral path.

A pacer 316 of FIG. 4 has a titanium casing 341. A cylindrical electrochemical cell 342 has small dimensions such as a diameter of about 14 millimeter and a length of about 24 millimeter. The positive terminal 343 of cell 342 is grounded to casing 341 through connector 344. The cell 342 is of the type having a lithium anode and utilizing thionyl chloride electrolyte. A negative terminal 345 of cell 342 is connected to circuit means 346 through a connector 347.

Particular attention is directed to the angular positioning of the axis 330 of the socket 322 of the pacer 316 of FIG. 4. Instead of the angle 331 of the axis 330 of socket 322 being at 90° with respect to end face 329, such angle is between about 30° and 60° and desirable about 45°. Because the socket 322 is thus angularly disposed, the lead 314 can be directed towards its spiral path without using a 90° elbow in plug 332.

Various modifications of the invention are possible without departing from the scope of the appended claims.

The invention claimed is:

1. In a cardiac pacer system having the combination of a lead, an electrode at the distal end, said electrode being adapted to contact a signal receiving zone of a heart, a plug at the proximal end of said lead, said plug fitting into a well of a socket in a cardiac pacer, a cardiac pacer, said cardiac pacer containing at least one electrochemical cell as a voltage source said cardiac pacer containing a circuitry unit comprising solid state electronic components, said socket of said pacer accommodating said plug at the proximal end of said lead delivering the output of the circuitry unit to said signal receiving zone of a heart, the improvement which consists essentially of:

plug positioning means directing said lead as a flat spiral around said cardiac pacer, said spiral initially being larger than required by the safe bending radius of the lead, whereby such spiral may contract to a relatively smaller spiral to accommodate to the greater distance between said cardiac pacer and said signal receiving zone as the body grows;

a bag having internal surfaces resistant to tissue growth, said bag permitting said contraction of said spiral because at least a significant portion of said spiral is within said bag;

means restricting movement of said cardiac pacer after implantation while permitting said contraction of the spiral portion of said lead; and said pacer and lead having dimensions adapted to permit implantation of said cardiac pacer as a pediatric pacer.

2. The cardiac pacer system of claim 1 in which the electrochemical cell employs the combination of a lithium anode and an electrolyte containing thionyl chloride.

3. The cardiac pacer system of claim 1 in which the cardiac pacer has a titanium casing.

4. The cardiac pacer system of claim 1 in which the bag has two openings accommodating the exterior of two portions of the spiral portion of the lead and the bag includes portions shaped to adjacent exterior portions of the cardiac pacer.

5. The cardiac pacer system of claim 1 in which the bag has a cradle system positioning the cardiac pacer in a central zone of the bag.

6. The cardiac pacer system of claim 1 in which an elbow plug participates in said positioning means directing said lead as a flat spiral.

7. The cardiac pacer system of claim 1 in which the angle of the axis of the socket with respect to the end face of the cardiac pacer is within the range of from 30° to 60° thereby participating in directing said lead as a flat spiral.

8. The cardiac pacer system of claim 1 in which the electrochemical cell employs the combination of a lithium anode and an electrolyte containing thionyl chloride and in which the cardiac pacer has a titanium casing and in which the bag has two openings accommodating the exterior of two portions of the spiral portion of the lead and the bag includes portions shaped to be adjacent exterior portions of the cardiac pacer and in which an elbow plug participates in said positioning means directing said lead as a flat spiral.

* * * * *